(12) United States Patent
Kuiper et al.

(10) Patent No.: US 9,976,185 B2
(45) Date of Patent: May 22, 2018

(54) CLASSIFIER FOR THE MOLECULAR CLASSIFICATION OF MULTIPLE MYELOMA

(75) Inventors: Rowan Kuiper, Rotterdam (NL); Pieter Sonneveld, Schiedam (NL)

(73) Assignee: ERASMUS UNIVERSITY MEDICAL CENTER ROTTERDAM, Rotterdam (NL)

( * ) Notice: Subject to any disclaimer, the term of this patent is extended or adjusted under 35 U.S.C. 154(b) by 142 days.

(21) Appl. No.: 14/232,176

(22) PCT Filed: Jul. 12, 2012

(86) PCT No.: PCT/EP2012/063722
§ 371 (c)(1),
(2), (4) Date: Mar. 19, 2014

(87) PCT Pub. No.: WO2013/007795
PCT Pub. Date: Jan. 17, 2013

(65) Prior Publication Data
US 2014/0221313 A1   Aug. 7, 2014

(30) Foreign Application Priority Data
Jul. 14, 2011   (EP) .................................... 11173971

(51) Int. Cl.
*C12Q 1/6886* (2018.01)
*C12Q 1/68* (2018.01)

(52) U.S. Cl.
CPC ......... *C12Q 1/6886* (2013.01); *C12Q 1/6837* (2013.01); *C12Q 2600/112* (2013.01); *C12Q 2600/118* (2013.01); *C12Q 2600/158* (2013.01)

(58) Field of Classification Search
None
See application file for complete search history.

(56) References Cited

U.S. PATENT DOCUMENTS

| 2007/0093969 A1* | 4/2007 | Mendrick ............ C12Q 1/6876 702/20 |
| 2008/0274911 A1 | 11/2008 | Burington et al. |

FOREIGN PATENT DOCUMENTS

| EP | 1964930 A1 | 3/2008 | |
| WO | 2010064016 A2 | 6/2010 | |
| WO | WO 2010151731 A1 * | 12/2010 | ........... C12Q 1/6886 |
| WO | 2013007795 A1 | 1/2013 | |

OTHER PUBLICATIONS

Broyl et al. Blood. 2010. 116(14): 2543-2553.*
Chng et al. Cancer Res. 2007. 67(7): 2982-2989.*
Zhan et al. Blood. 2006. 108(6): 2020-2028.*
Slonin. Nature Genetics Supplement. 2002. 32; 502-508.*
Michiels et al. Lancet. 2005. 365:488-492.*
Moreau et al. Blood. 2012. 120(5): 947-959.*
Bolstad et al. Bioinformatics. 2003. 19(2): 185-193.*
Chou et al. Nucleic acids Research. 2004. 32(12): e99.*
International Search Report and Written Opinion for International Application No. PCT/EP2012/063722, dated Nov. 8, 2012, 12 pages.
Decaux et al., "Prediction of survival in multiple myeloma based on gene expression profiles reveals cell cycle and chromosomal instability signatures in high-risk patients and hyperdiploid signatures in low-risk patients: a study of the Intergroupe Francophone du Myélome," Journal of Clinical Oncology, vol. 26, No. 29, Oct. 10, 2008, pp. 4798-4805.
PCT International Preliminary Report on Patentability, PCT/EP2012/063722 dated Jan. 14, 2014.
Dickens et al., Homozygous Deletion Mapping in Myeloma Samples Identifies Genes and an Expression Signature Relevant to Pathogenesis and Outcome, Clin Cancer Res., Mar. 2010, pp. 1856-1864, vol. 16, No. 6.
Rapaport et al., Comprehensive evaluation of differential gene expression analysis methods for RNA-seq data, Genome Biology, 2013, 14:R95.
Shaughnessy Jr., et al., A validated gene expression model of high risk multiple myeloma is defined by deregulated expression of genes mapping to chromosome 1, Blood, pp. 2276-2284, vol. 109, The American Society of Hematology, Washington DC.
Bair et al., Prediction by Supervised Principal Components, Journal of the American Statistical Association, Mar. 2006, pp. 119-137, vol. 101, No. 473.
Eleveld-Trancikova et al, Translocation t(4;14) retains prognostic significance even in the setting of high-risk molecular signature, Leukemia, Sep. 6, 2007, 22, pp. 459-461.
Communication from European Patent Office for Patent Application No. 12 733 765.7 dated Dec. 5, 2014.
Chng et al., Translocation t(4;14) retains prognostic significance even in the setting of high-risk molecular signature, Leukemia, 2008, pp. 459-461, vol. 22, doi:10.1038/sj.leu.2404934; published online Sep. 6, 2007.

* cited by examiner

*Primary Examiner* — Joseph G. Dauner
(74) *Attorney, Agent, or Firm* — TraskBritt, P.C.

(57) ABSTRACT

The present invention is in the field of molecular diagnostics and relates to a method for classifying samples obtained from patients diagnosed with multiple myeloma into three newly defined clusters. The invention also relates to a method for determining the prognosis of an individual diagnosed with multiple myeloma as well as a method for the prediction of the response to treatment of an individual diagnosed with multiple myeloma. More in particular, the invention provides a method for determining the disease outcome or the prognosis of a patient diagnosed with multiple myeloma by classifying said patient into a high risk or a low risk category, based on a 92 gene classifier.

3 Claims, 5 Drawing Sheets

CLASSIFIER FOR THE MOLECULAR CLASSIFICATION OF MULTIPLE MYELOMA

INTRODUCTION

The present invention is in the field of molecular diagnostics and relates to a method for classifying samples obtained from patients diagnosed with multiple myeloma. The invention also relates to a method for determining the prognosis of an individual diagnosed with multiple myeloma as well as a method for the prediction of the response to treatment of an individual diagnosed with multiple myeloma.

BACKGROUND OF THE INVENTION

Multiple myeloma (MM) is characterized by accumulation of malignant monoclonal plasma cells in the bone marrow. Median overall survival (OS) is 3 to 4 years but varies widely between patients. Currently, the International Staging System (ISS), based on serum β2m and albumin is clinically widely used to classify MM patients into three prognostic categories. [1]

Based on cytogenetics, two classes of MM can be distinguished with implications for MM biology and prognosis. Hyperdiploid MM, ~60% of patients, characterized by trisomies of multiple odd chromosomes (3, 5, 7, 9, 11, 15, 19, and 21) has a relatively good prognosis. Non-hyperdiploid MM, ~40% of cases, is characterized by recurrent translocations involving the immunoglobulin heavy chain gene at 14q32, resulting in transcriptional activation of CCND1, CCND3, MAF, MAFB, or FGFR3/MMSET. [2, 3] Translocation t(11;14), involving CCND1, confers a relatively favourable prognosis whereas translocation t(4;14), involving FGFR3 and MMSET, has poor prognosis. [4, 5] The translocations t(14;16) and t(14;20), involving the MAF oncogenes also confer a poor prognosis, although recently this has been debated [6]. In addition, del(17p), del(13q) and 1q-gain detected with conventional karyotyping were reported to be associated with poor prognosis. [7]

Based on gene expression analysis, a number of classifications for MM have been published which include the University of Arkansas for Medical Sciences (UAMS) classification and more recently a classification by our own group. The UAMS molecular classification of myeloma consists of seven distinct gene expression clusters, including translocation clusters MS, MF, and CD-1/2, as well as a hyperdiploid cluster (HY), a cluster with proliferation-associated genes (PR), and a cluster characterized by low percentage of bone disease (LB). [8] Our classification of MM resulted in three additional clusters: NFκB, CTA and PRL3. [9]

Gene expression is able to explain an even larger amount of variance in survival compared to ISS and cytogenetics. One of the first survival signatures based on gene expression was the UAMS-70-gene classifier, and the further refined UAMS-17-gene classifier. [10, 11]. Other classifiers include the Millennium signature, the MRC-IX-6-gene signature, and the IFM classifier. [12-14] In addition signatures were reported to predict plasma cell proliferation such as the recently published gene expression proliferation index (GPI). [15]

The aim of this study was to develop a prognostic signature, based upon gene expression profiles (GEPs) of MM patients, treated with either standard induction treatment or bortezomib induction, followed in both cases by high-dose melphalan and maintenance.

SUMMARY OF THE INVENTION

We present herein a classifier comprising a 92 gene set capable of distinguishing between patients with a high risk and patients with a low risk. In a survival analysis of newly diagnosed multiple myeloma (MM) patients, the classifier yielded excellent results wherein the classification in the low risk group identified patients with a good overall survival, whereas the group identified as high risk showed significantly worse overall survival rates.

The invention therefore relates to a method for determining the disease outcome or the prognosis of a patient diagnosed with multiple myeloma by classifying said patient into a high risk or a low risk category, said method comprising the steps of a) providing a gene chip comprising probes for the detection of at least the 92 gene set according to table 1, b) contacting the gene chip with a sample comprising mRNA from a patient, c) determining the expression levels of the 92 gene set in the sample, d) normalizing the expression levels using mean/variance normalization in order to obtain the normalized expression value e) multiply the normalized expression value with the beta value according to table 1 to obtain the calculated value for an individual probe, f) determine an EMC-92 score by summation of the calculated values of the individual probes, wherein an EMC-92 score above a predetermined threshold indicates that the patient is to be classified in the high risk category and a score at or below the predetermined threshold indicates that the patient is to be classified in the low risk category.

DETAILED DESCRIPTION OF THE INVENTION

We present herein a classifier comprising a 92 gene set capable of distinguishing between patients with a high risk and patients with a low risk. In a survival analysis of newly diagnosed multiple myeloma (MM) patients, the classifier yielded excellent results wherein the classification in the low risk group identified patients with a good overall survival, whereas the group identified as high risk showed significantly worse overall survival rates.

The classifier was validated in an experimental setting wherein patients with poor overall survival (OS) were distinguished from patients with standard OS. Therefore, an SPCA model was built using the HOVON65/GMMG-HD4 data as a training set (see the experimental section below). A number of 1088 probe sets were found to be associated with progression-free survival (PFS) in a univariate Cox regression analysis (FDR<10%). Based on these probe sets, we developed a classifier with 92 probe sets (table 1). This classifier will be termed the EMC-92-gene signature.

TABLE 1

| # | Probes | Beta | Gene | Chromosome | Band |
|---|---|---|---|---|---|
| 1 | 226217_at | −0.0319 | SLC30A7 | 1 | p21.2 |
| 2 | 208967_s_at | 0.0113 | AK2 | 1 | p35.1 |
| 3 | 202553_s_at | 0.0054 | SYF2 | 1 | p36.11 |
| 4 | 217728_at | 0.0773 | S100A6 | 1 | q21.3 |
| 5 | 223381_at | −0.0070 | NUF2 | 1 | q23.3 |
| 6 | 218365_s_at | 0.0035 | DARS2 | 1 | q25.1 |
| 7 | 211963_s_at | 0.0303 | ARPC5 | 1 | q25.3 |
| 8 | 222680_s_at | 0.0205 | DTL | 1 | q32.3 |
| 9 | 221826_at | 0.0200 | ANGEL2 | 1 | q32.3 |

TABLE 1-continued

| # | Probes | Beta | Gene | Chromosome | Band |
|---|---|---|---|---|---|
| 10 | 201795_at | 0.0067 | LBR | 1 | q42.12 |
| 11 | 202813_at | 0.0548 | TARBP1 | 1 | q42.2 |
| 12 | 202322_s_at | 0.0129 | GGPS1 | 1 | q42.3 |
| 13 | 202728_s_at | −0.1105 | LTBP1 | 2 | p22.3 |
| 14 | 209683_at | −0.0561 | FAM49A | 2 | p24.2 |
| 15 | 201930_at | −0.0090 | MCM6 | 2 | q21.3 |
| 16 | 228416_at | −0.0778 | ACVR2A | 2 | q22.3 |
| 17 | 206204_at | 0.0477 | GRB14 | 2 | q24.3 |
| 18 | 215177_s_at | −0.0768 | ITGA6 | 2 | q31.1 |
| 19 | 224009_x_at | −0.0520 | DHRS9 | 2 | q31.1 |
| 20 | AFFX-HUMISGF3A/M97935_MA_at | 0.0525 | STAT1 | 2 | q32.2 |
| 21 | 222154_s_at | 0.0154 | SPATS2L | 2 | q33.1 |
| 22 | 207618_s_at | 0.0746 | BCS1L | 2 | q35 |
| 23 | 239054_at | −0.1088 | SFMBT1 | 3 | p21.1 |
| 24 | 217852_s_at | 0.0008 | ARL8B | 3 | p26.1 |
| 25 | 219510_at | −0.0097 | POLQ | 3 | q13.33 |
| 26 | 202107_at | 0.0225 | MCM2 | 3 | q21.3 |
| 27 | 220351_at | 0.0420 | CCRL1 | 3 | q22.1 |
| 28 | 208942_s_at | −0.0997 | SEC62 | 3 | q26.2 |
| 29 | 233437_at | 0.0446 | GABRA4 | 4 | p12 |
| 30 | 225366_at | 0.0140 | PGM2 | 4 | p14 |
| 31 | 218662_s_at | −0.0176 | NCAPG | 4 | p15.31 |
| 32 | 204379_s_at | 0.0594 | FGFR3 | 4 | p16.3 |
| 33 | 201307_at | 0.0165 | SEPT11 | 4 | q21.1 |
| 34 | 202542_s_at | 0.0870 | AIMP1 | 4 | q24 |
| 35 | 205046_at | 0.0087 | CENPE | 4 | q24 |
| 36 | 226218_at | −0.0644 | IL7R | 5 | p13.2 |
| 37 | 202532_s_at | −0.0006 | DHFR | 5 | q14.1 |
| 38 | 226742_at | −0.0345 | SAR1B | 5 | q31.1 |
| 39 | 231738_at | 0.0686 | PCDHB7 | 5 | q31.3 |
| 40 | 214150_x_at | −0.0349 | ATP6V0E1 | 5 | q35.1 |
| 41 | 201555_at | −0.0052 | MCM3 | 6 | p12.2 |
| 42 | 209026_x_at | 0.0255 | TUBB | 6 | p21.33 |
| 43 | 211714_x_at | 0.0221 | TUBB | 6 | p21.33 |
| 44 | 213002_at | −0.0418 | MARCKS | 6 | p22.2 |
| 45 | 221041_s_at | −0.0520 | SLC17A5 | 6 | q13 |
| 46 | 217824_at | −0.0041 | NCUBE1 | 6 | q15 |
| 47 | 223811_s_at | 0.0556 | SUN1/GET4 | 7 | p22.3 |
| 48 | 202842_s_at | −0.0626 | DNAJB9 | 7 | q31.1 |
| 49 | 208232_x_at | −0.0493 | Unknown | 8 | p12 |
| 50 | 208732_at | −0.0618 | RAB2A | 8 | q12.1 |
| 51 | 201398_s_at | −0.0254 | TRAM1 | 8 | q13.3 |
| 52 | 233399_x_at | −0.0184 | ZNF252 | 8 | q24.3 |
| 53 | 200775_s_at | 0.0163 | HNRNPK | 9 | q21.32 |
| 54 | 230034_x_at | −0.0330 | MRPL41 | 9 | q34.3 |
| 55 | 204026_s_at | 0.0046 | ZWINT | 10 | q21.1 |
| 56 | 243018_at | 0.0407 | Unknown | 11 | p14.1 |
| 57 | 222713_s_at | 0.0278 | FANCF | 11 | p14.3 |
| 58 | 221755_at | 0.0396 | EHBP1L1 | 11 | q13.1 |
| 59 | 231210_at | 0.0093 | C11orf85 | 11 | q13.1 |
| 60 | 202884_s_at | 0.0714 | PPP2R1B | 11 | q23.1 |
| 61 | 219550_at | 0.0559 | ROBO3 | 11 | q24.2 |
| 62 | 238780_s_at | −0.0529 | Unknown | 11 | q24.3 |
| 63 | 208747_s_at | −0.0874 | C1S | 12 | p13.31 |
| 64 | 38158_at | 0.0423 | ESPL1 | 12 | q13.13 |
| 65 | 217732_s_at | −0.0252 | ITM2B | 13 | q14.2 |
| 66 | 214482_at | 0.0861 | ZBTB25 | 14 | q23.3 |
| 67 | 200701_at | −0.0210 | NPC2 | 14 | q24.3 |
| 68 | 238662_at | 0.0490 | ATPBD4 | 15 | q14 |
| 69 | 217548_at | −0.0423 | C15orf38 | 15 | q26.1 |
| 70 | 213007_at | −0.0106 | FANCI | 15 | q26.1 |
| 71 | 231989_s_at | 0.0730 | SMG1 | 16 | p12.3 |
| 72 | 238116_at | 0.0661 | DYNLRB2 | 16 | q23.2 |
| 73 | 212282_at | 0.0530 | TMEM97 | 17 | q11.2 |
| 74 | 203145_at | −0.0002 | SPAG5 | 17 | q11.2 |
| 75 | 201292_at | −0.0372 | TOP2A | 17 | q21.2 |
| 76 | 210334_x_at | 0.0175 | BIRC5 | 17 | q25.3 |
| 77 | 212055_at | 0.0384 | C18orf10 | 18 | q12.2 |
| 78 | 242180_at | −0.0585 | TSPAN16 | 19 | p13.2 |
| 79 | 208904_s_at | −0.0334 | RPS28 | 19 | p13.2 |
| 80 | 213350_at | 0.0056 | RPS11 | 19 | q13.3 |
| 81 | 200875_s_at | 0.0437 | NOP56 | 20 | p13 |
| 82 | 212788_x_at | −0.0164 | FTL | 19 | p13 |
| 83 | 215181_at | −0.0342 | CDH22 | 20 | q13.12 |
| 84 | 221677_s_at | 0.0126 | DONSON | 21 | q22.11 |
| 85 | 201102_s_at | 0.0349 | PFKL | 21 | q22.3 |
| 86 | 208667_s_at | −0.0390 | ST13 | 22 | q13.2 |
| 87 | 216473_x_at | −0.0576 | DUX4 | 4/10 | q35.2/q26.3 |
| 88 | 200933_x_at | −0.0323 | RPS4X | X | q13.1 |
| 89 | 218355_at | 0.0116 | KIF4A | X | q13.1 |
| 90 | 221606_s_at | 0.0208 | HMGN5 | X | q21.1 |
| 91 | 225601_at | 0.0750 | HMGB3 | X | q28 |
| 92 | 214612_x_at | 0.0496 | MAGEA6 | X | q28 |

Figure 1A:
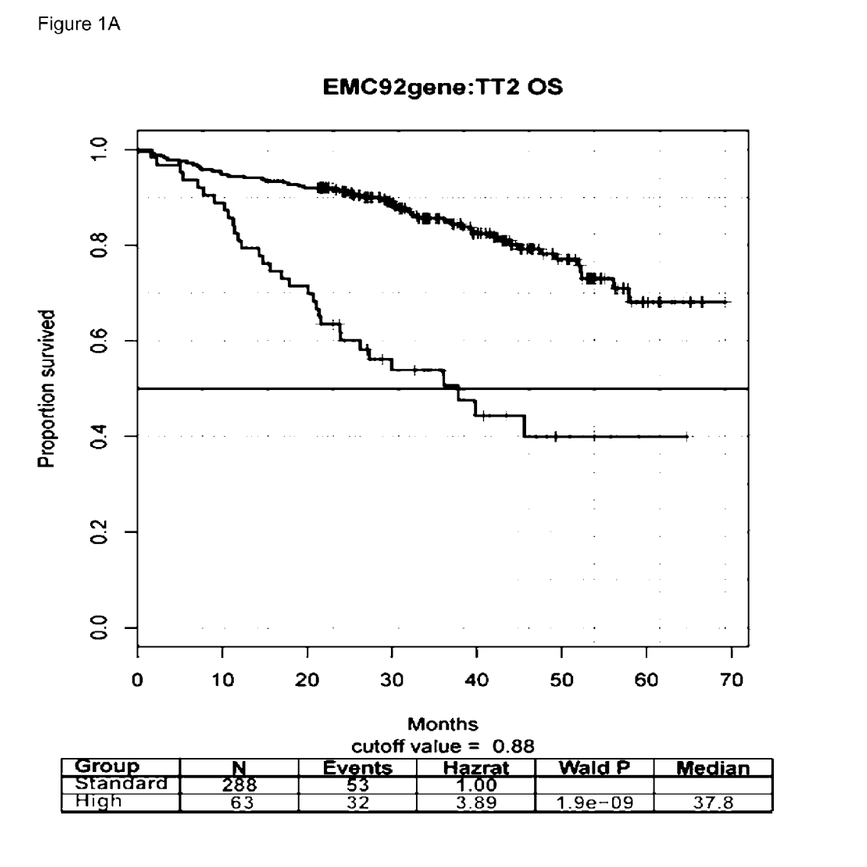
Figure 1B:
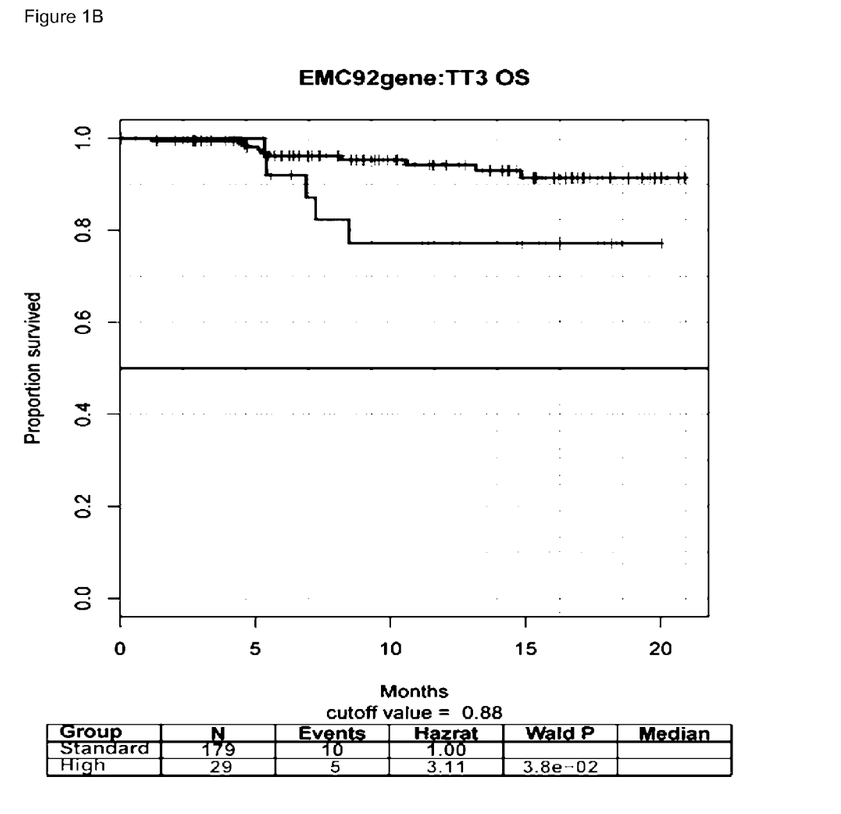
Figure 1C:
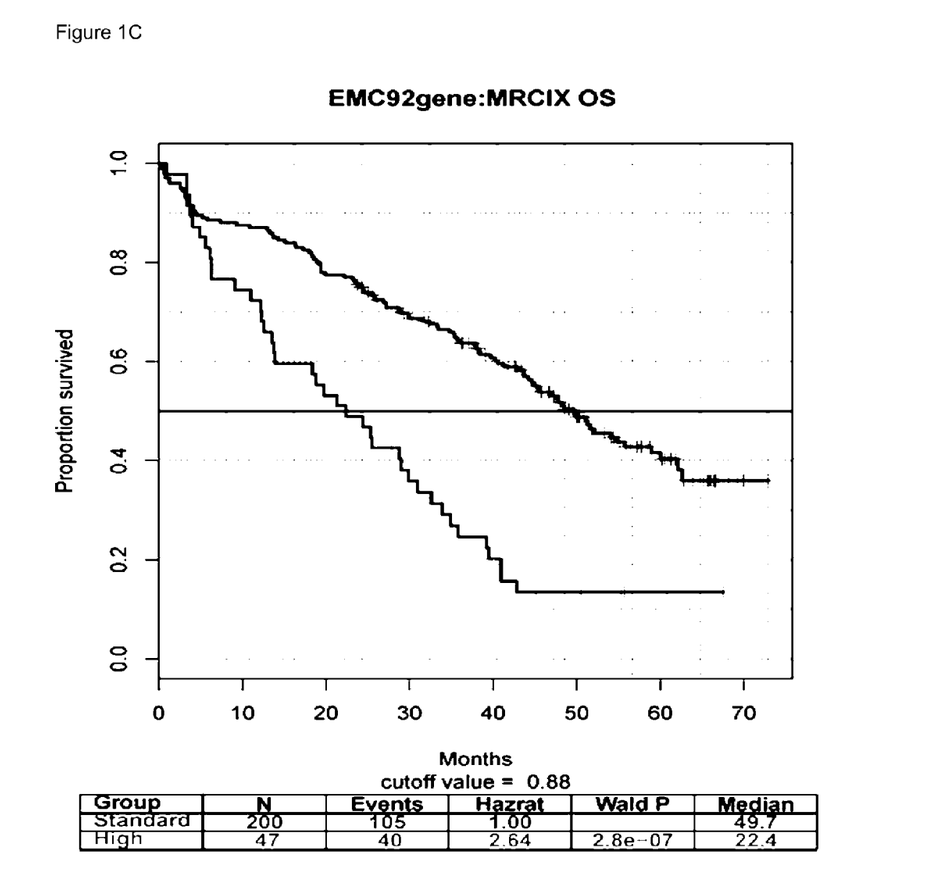
Figure 1D:
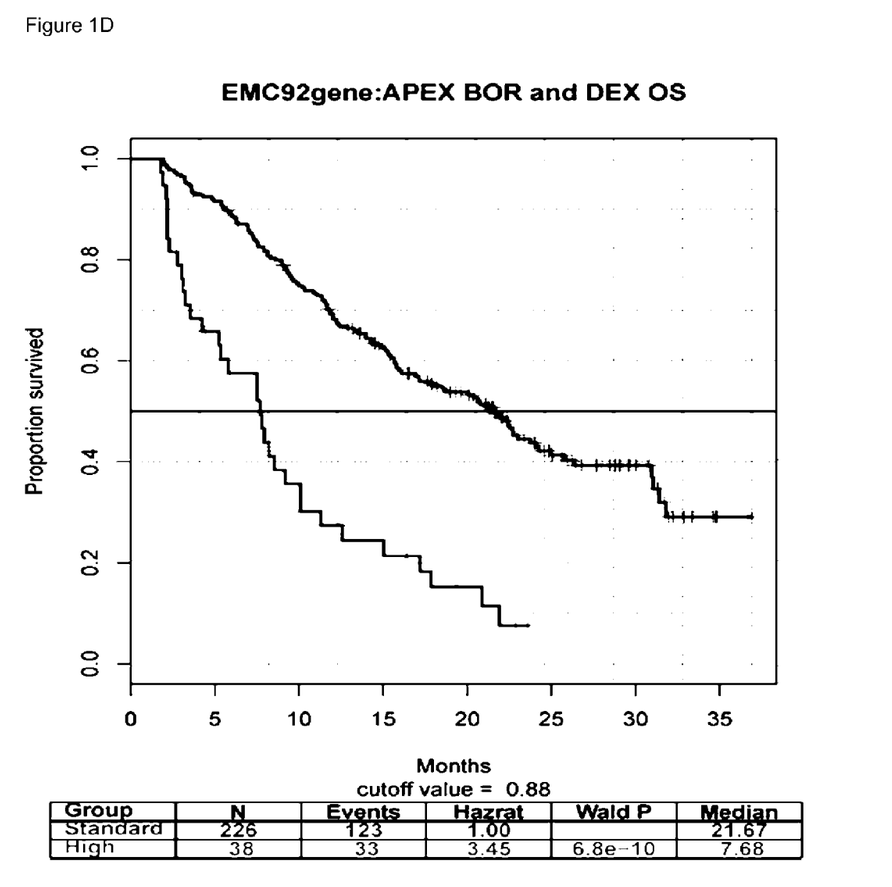

A dichotomizing cut-off threshold was based on the clinically relevant definition of high-risk patients as those patients who have an overall survival of less than 2 years. This amounted to a proportion of 21.7% in the training set and a cut-off value of 0.827. Within all four data sets TT2(n=351)[11], TT3(n=208)[11], MRC-IX(n=247)[14] and APEX(n=264)[12] the EMC-92-gene signature discriminated a high-risk group, which was significantly set apart from the standard-risk group (FIGS. 1a to d).

In datasets containing newly diagnosed patients, the EMC-92-gene signature selected a high-risk population of 17.7% on average, with a significantly shorter OS and hazard-ratios of 3.52 ($p=2.5 \times 10^{-8}$=;TT2), 2.7 ($p=0.07=^2$; TT3) and 2.38 ($p=3.6 \times 10^{-6}$=;MRC-IX). In the relapse setting the EMC-92-gene signature also filtered out high-risk patients with a large hazard-ratio of 3.14 ($p=5.3 \times 10^{-9}$=; APEX). The proportion of high-risk patients in this latter study was lower compared to the MRC-IX and TT2 studies, but not significantly (15.9%, n=264 vs. 19.6%, n=; p=0.2) (Table 1.1).

In a multivariate covariant analysis the EMC-92-gene signature was independent of most standard prognostic factors and clinical characteristics. Three datasets were available for this analysis: HOVON65/GMMG-HD4, APEX and MRC-IX. Multivariate analysis on the HOVON65/GMMG-HD4 study demonstrates that together with the EMC-92-signature, del(17p), $\beta_2m[\geq 3.5$ mg/L] and allogenic transplantation were significantly related to shorter survival, whereas WHO status [0] was found to be significantly related to longer survival. In the APEX, albumin level, ISS and IgG isotype were found to be significantly related. For the MRC-IX, mainly ISS related covariants were found. WHO[2], 1 q gain and IGHsplit showed a clear contribution. IGHsplit indicates all patients with cytogenetic aberration of the IGH locus. Age had a small but significant hazard-ratio here. In all three datasets the EMC-92-gene signature remained a strong predictor for survival after correction for available variables.

The samples in all four validation sets were assigned a molecular cluster label by nearest neighbor classification. Logistic regression for association between the molecular clusters and high-risk outcome revealed a significant relation between high-risk classification and the MF, MS, PR and HY clusters.

Comparing the UAMS-17-gene and EMC-92-gene set in independent datasets (i. E. TT3, MRC-IX and APEX), a significantly higher proportion of patients was classified as high-risk by the EMC-92-gene signature (p=0.009). Moreover the estimated hazard-ratios (high-risk/standard-risk) were higher in the EMC-92-gene classifier with the exception of the TT3 study.

In the MRCIX study population, the EMC-92 gene classifier exclusively identified 31 patients correctly as high risk patients, which were missed by the UAMS-17 gene classifier (50% survival rate of 11, 24 and 51 months for the shared high risk group, intermediate high risk group and standard risk groups, respectively). Moreover, the UAMS-17 gene classifier exclusively identified 10 patients as high risk patients with a lower hazard ratio as compared to the 31 patients classified as high-risk by the EMC92 gene classifier.

The superiority of the EMC-92 classifier was even clearer in the APEX population. Here, 24 patients were exclusively identified as high risk in the EMC-92 classifier, which were missed in the UAMS-17 classifier. These 24 patients formed a group whose overall survival after 20 months was 14% whereas the high risk population identified in both the EMC-92 and UAMS-17 classifier showed an overall survival of 25% after 20 months.

In addition, the UAMS-70-gene, MRC-IX-6-gene signature, GPI score, the Millennium and IFM signature were applied to the datasets. In a pair wise multivariate analysis based on the pooled independent datasets, including two classifiers at a time and correcting for study and age, the EMC-92 gene classifier had the highest hazard ratios and lowest p values of all classifiers.

The intersection of high-risk patients between the EMC-92-gene and UAMS-17-gene classifiers was ~8% of the total population. About 14% of patients were classified as high-risk by either one of these classifiers. The intersecting high-risk group showed the largest differences compared to the intersecting standard-risk group as indicated by the hazard-ratios (HR=5.40; $p=3.1 \times 10^{-3}$; TT3), (HR=3.84; $p=5 \times 10^{-7}$; MRC-IX) and (HR=3.39; $p=1.9 \times 10^{-5}$; APEX). The 14% of patients uniquely classified as high-risk by either signature, showed an intermediate hazard-ratio. For the UAMS-17-gene high-risk group this resulted in hazard-ratios of 4.08($p=7.6 \times 10^{-2}$), 1.92($p=7.7 \times 10^{-2}$) and 2.31 ($p=2.3 \times 10^{-2}$) for the TT3, MRX-IX and APEX. The EMC-92-gene high-risk group gave hazard-ratios of 0 ($p=1.0$ no events), 1.98($p=2.9 \times 10^{-34}$) and 3.21 ($p=1.6 \times 10^{-6}$) for the TT3, MRX-IX and APEX.

In clinical practice, prognosis of MM patients is mainly based on ISS-stage and interphase fluorescence in situ hybridization (FISH). Several chromosomal aberrations detected by FISH have prognostic implications [25]. Del (17p) is considered the most important, associated with unfavorable outcome and present in 9% of patients [26, 27]. Still 60% of patients with this deletion do not display a specific poor outcome [28]. The combination of chromosomal aberration, t(4;14), del(17p) and ISS have further delineated patients with a poor prognosis [29].

Previously, in the UAMS classification, the MS, MF and PR clusters showed lower PFS and OS, whereas clusters HY, LB, CD-1 and CD-2 were associated with longer PFS and OS [8]. Here, we evaluated the variability in PFS and OS in the GEP-based clusters of the HOVON65 classification. VAD treated patients demonstrate significant differences in PFS and OS between clusters with a clearly reduced survival for the MF subgroup, whereas in bortezomib (PAD) treated patients no significant difference were found.

Bortezomib based treatment has been shown to overcome certain adverse prognostic markers such as del(13q) resulting in better PFS and OS in patients with poor prognostic markers such as ISS-3, del(17p), and t(4;14) [16]. Both chromosomal markers and the HOVON65 GEP based classification vary with treatment and are not applicable for diagnosing high-risk patients accurately. Therefore, a high-risk GEP signature was developed.

Previous classifiers include the UAMS-17/70-gene and MRC-IX-6-gene classifiers, both capable of predicting in independent datasets [11, 14]. In contrast, the Millennium and the IFM signatures demonstrate less solid performance in independent validation sets [12, 13].

The EMC-92 gene expression signature presented herein, is highly discriminative for patients with high-risk versus standard-risk MM across different (induction) regimes. Validation in UAMS TT2 (thalidomide-based) [17], TT3(bortezomib-based) [18] and MRC-IX trial (thalidomide maintenance in both young and elderly patients) [19, 20] showed high performance in these independent test environments. This is true for both the continuous fit of the model—which is a goodness-of-fit indicator—as well as the dichotomized output into high-risk/standard-risk which is a requirement for practical use in a clinical setting.

In multivariate analyses, the EMC-92-gene high-risk signature remains a strong predictor for early death. Still there is strong evidence that ISS staging (serum albumin and $\beta_2 m$ levels) turns out to be another major contributor for explaining survival related variance in the presence of the signature. Therefore incorporating ISS into the signature could potentially lead to an even better prediction of survival.

Patients classified as high-risk are overrepresented within the molecular MF, MS and PR clusters and underrepresented within the HY cluster. This correlates well with previous data: HY represents hyperdiploid patients with a generally favourable prognosis; on the other hand, MS and MF represent patients with translocations t(4;14) and t(14;16/20) which are usually though to have an unfavorable prognosis. Finally, PR represents the proliferation cluster, which was shown to be associated with poor prognosis [8, 11, 15]. In relation to this, pathway analysis of the EMC-92-gene signature demonstrated cell cycle regulation to be among the main functions found.

In the EMC-92-gene signature as well as the set of genes linked to survival in the univariate analysis, chromosomal location of 1q was highly enriched (table 1) as was previously shown for the UAMS-17-gene signature [11]. Also probe sets located on chromosome 4 are enriched. These probe sets were found to be scattered over the entire chromosome and not only at the distal end of the p arm where MMSET and FGFR3 are located. Chromosome 4 has previously not been considered a risk factor, but a low frequency of multiple gains and/or losses affecting this chromosome has been reported [30].

The EMC-92-gene signature was compared in a multivariable analysis to the UAMS-17/70-gene, MRC-IX-6-gene, GPI score, IFM and Millennium classifiers. Three pooled datasets were formed from publicly available MM datasets, allowing an independent comparison of the signatures that were not trained on those datasets (Kuiper, R. et al., Leukemia 2012, 1-8 incorporated herein by reference). The outputs from the signatures were input into a Cox proportional hazards model, see Table 2. In all three comparisons, the EMC-92 signature obtained the most significant hazard ratio (HR), and thus is the most relevant prognostic factor of all signatures (including the UAMS-70 from Signal Genetics).

TABLE 2

Comparison of EMC 92 with conventional tests (HR = hazard ratio)

| | Datasets pooled | Signature | HR | P-value |
|---|---|---|---|---|
| Comparison 1 | MRCIX + APEX + TT3 | SKY92[11] | 1.75 | 4.60E−04 |
| | | UAMS17[10] | 1.22 | 3.30E−01 |
| | | UAMS70[10] | 1.80 | 1.10E−03 |
| | | IFM15[12] | 1.25 | 9.10E−02 |

TABLE 2-continued

Comparison of EMC 92 with conventional
tests (HR = hazard ratio)

|  | Datasets pooled | Signature | HR | P-value |
|---|---|---|---|---|
| Comparison 2 | APEX + TT2 + TT3 | SKY92 MRCIX6[13] IFM15 | 2.53 1.50 1.38 | 3.70E−09 4.10E−03 2.50E−02 |
| Comparison 3 | MRCIX + TT2 + TT3 | SKY92 Millennium100[14] IFM15 | 2.95 0.81 1.13 | 5.60E−12 1.30E−01 4.00E−01 |

The EMC-92-gene signature turns out to have the best dichotomized performance on its validation sets. Moreover, in comparison to other classifiers the proportion of high-risk patients is higher. One would expect that differences between high-risk and standard-risk become less pronounced as the high-risk proportion increases. It should be mentioned that even at this high proportion, differences in survival time are larger for the EMC-92 as compared to other classifiers selecting smaller risk groups.

In a multivariate analysis combining the signatures, the EMC-92-gene signature had the strongest discriminative ability.

In conclusion, we developed a high-risk signature highly discriminative for patients with high-risk versus standard-risk MM, irrespective of treatment regime, age and relapse setting. Use of this signature in the clinical setting may lead to a more informed treatment choice and potentially better outcome for the patient.

In conclusion, our study concerns the development of a robust high-risk signature, incorporates most known prognostic markers, clinical, cytogenetic and GEP based, and shows the developed EMC-92-gene signature to be the strongest independent prognostic marker for poor survival known. This EMC-92-gene signature is able to select out a high-risk group of MM patients for whom in the future alternative, more intensive treatments should be sought.

Hence, the invention relates to a method for determining the disease outcome or the prognosis of a patient diagnosed with multiple myeloma by classifying said patient into a high risk or a low risk category, said method comprising the steps of
 a) providing a gene chip comprising probes for the detection of at least the 92 gene set according to table 1,
 b) contacting the gene chip with a sample comprising mRNA from a patient,
 c) determining the expression levels of the 92 gene set in the sample,
 d) normalizing the expression levels using mean/variance normalization in order to obtain the normalized expression value,
 e) multiply the normalized expression value with the beta value according to table 1 to obtain the calculated value for an individual probe,
 f) determine an EMC-92 score by summation of the calculated values of the individual probes,
 wherein an EMC-92 score above a predetermined threshold indicates that the patient is to be classified in the high risk category and a score at or below the threshold indicates that the patient is to be classified in the low risk category.

As further detailed herein, a preferred threshold value is at least 0.75, especially preferred is a threshold value of 0.827.

In summary, we report herein on the generation and validation of the EMC-92 signature, which was based on the HOVON65/GMMG-HD4 clinical trial. Conventional prognostic markers such as ISS stage and adverse cytogenetics have been augmented by signatures based on gene expression in order to increase accuracy in outcome prediction in MM. More accurate prognosis may lead to the development of treatment schedules that are specifically aimed at improving survival of high-risk MM patients.

For clinical relevance, a signature must have both the ability to separate risk groups as clearly as possible and to predict stable groups of relevant size. The EMC-92 signature meets both criteria. In all validation sets a high-risk group of patients can be significantly determined and the proportion of high-risk patients is stable across the validation sets. The validation sets represent different drug regimens, including thalidomide (MRC-IX, TT2) and bortezomib (APEX, TT3). Also, the signature is relevant to both transplant-eligible (for example, TT3) and non-transplant-eligible patients (subset of MRC-IX), as well as newly diagnosed (for example, TT2) and relapsed patients (APEX). In contrast, the predictions of the IFM-15 and MILLENNIUM-100 signatures in the validation sets fail to reach significance in independent data sets such as MRC-IX and TT3.

In conclusion, we have developed a risk signature that is highly discriminative for patients with high-risk vs standard-risk MM, irrespective of treatment regime, age and relapse setting. Use of this signature in the clinical setting may lead to a more informed treatment choice and potentially better outcome for the patient.

LEGEND TO THE FIGURES

FIG. 1 Performance of the EMC-92 classifier in predicting overall survival. High risk signature on four validation sets with a fixed cut-off value of 0.827. A: UAMS Total Therapy 2. B: UAMS Total Therapy 3. C: MRC-IX. D: APEX.

EXAMPLES

Example 1: Patients

Five previously described datasets were used, of which both survival as well as GEPs of purified plasma cells obtained from bone marrow aspirates of myeloma patients, were available. These are HOVON65/GMMG-HD4 (N=320)(GSE19784) [9], Total Therapy 2 (TT2)(n=351) [11], TT3 (n=208)(GSE2658) [11], MRC-IX (n=247) (GSE15695) [14], and APEX (n=264)(GSE9782) [12].

The HOVON65/GMMG-HD4 data was used as a training set. This multicenter trial compared the efficacy of bortezomib (PAD) to standard treatment (VAD) in newly diagnosed patients. Patients were randomized to induction treatment with three VAD or PAD cycles [16] For a total of 290 patients both follow-up and GEPs were available [9].

The other four independent datasets were used as validation. Two datasets, TT2 and TT3, were derived from clinical trials performed in newly diagnosed patients both treated with a complex regimen. The first was a randomized prospective treatment trial in which patients were randomly assigned to receive or not to receive thalidomide during all phases of treatment [17]. The latter, was carried out by the same group according to the same regimen but with the addition of bortezomib to the thalidomide arm [18]. TT3 is a very small set with only 15 OS events but is included here for completeness.

The MRC-IX trial included both younger and older newly diagnosed patients. For younger patients treatment consisted of induction with vincristine or no vincristine followed by transplantation. Older patients were treated initially with a thalidomide vs. melphalan based treatment. Maintenance for both young and old patients was a comparison of thalidomide vs. no thalidomide[19, 20]. The trial and dataset denoted here as APEX consisted of the three trials APEX, SUMMIT and CREST. These trials aimed at testing the efficacy of bortezomib in relapse cases [21-23].

The IFM dataset on which the IFM signature was based has not been evaluated due to an incompatible GEP platform [13].

Example 2: Gene Expression Analysis

Two types of Affymetrix gene expression platforms were used. The Affymetrix GeneChip® Human Genome U133 Plus 2.0 Array was used in the HOVON65/GMMG-HD4, TT2, TT3 and MRC-IX whereas Affymetrix HG U133 NB chips was used in the APEX study. To allow for validation across different studies, only probe sets present on both platforms were included. A lower probe set expression boundary was set to the 5% lowest expression for the bioB hybridization controls in the HOVON65/GMMG-HD4 set. Probe sets with a lower expression in ≥95% of the HOVON65/GMMG-HD4 patients were excluded. All data were MASS normalized, $\log_2$ transformed and mean-variance scaled.

The HOVON65/GMMG-HD4 molecular classification was performed previously [9]. To assign a cluster label to new validation samples, an Euclidean nearest neighbor algorithm was used with HOVON65/GMMG-HD4 being the reference set.

The HOVON65/GMMG-HD4 was used as a training set for building a GEP based survival classifier. The model was built using a Supervised Principal Component Analysis (SPCA) framework. All calculations were performed in the R statistical environment using the survival package for survival analysis. The maxstat package was used to determine the optimal cut-off value for high-risk.

Data were analyzed using Ingenuity Pathway Analysis (Ingenuity Systems®, www. Ingenuity. Com). Both the gene set corresponding to the SPCA based survival classifier as well as the gene set generated by the initial univariate ranking (FDR<10%) were analyzed. Probe sets present in both the HG U133 Plus 2.0 and NB platforms were used as a reference. P-values were derived from right-tailed Fisher exact tests corrected for multiple testing using Benjamini Hochberg correction.

Example 3: Comparison with Published Gene Signatures

We set out to evaluate the performance of the EMC-92 signature in relation to available GEP-based prognostic signatures for OS in MM. To this end, the following signatures were evaluated: UAMS-70, UAMS-17, UAMS-80, IFM-15, gene proliferation index (GPI-50), MRC-IX-6 and MILLENNIUM-100.

Figure 2:
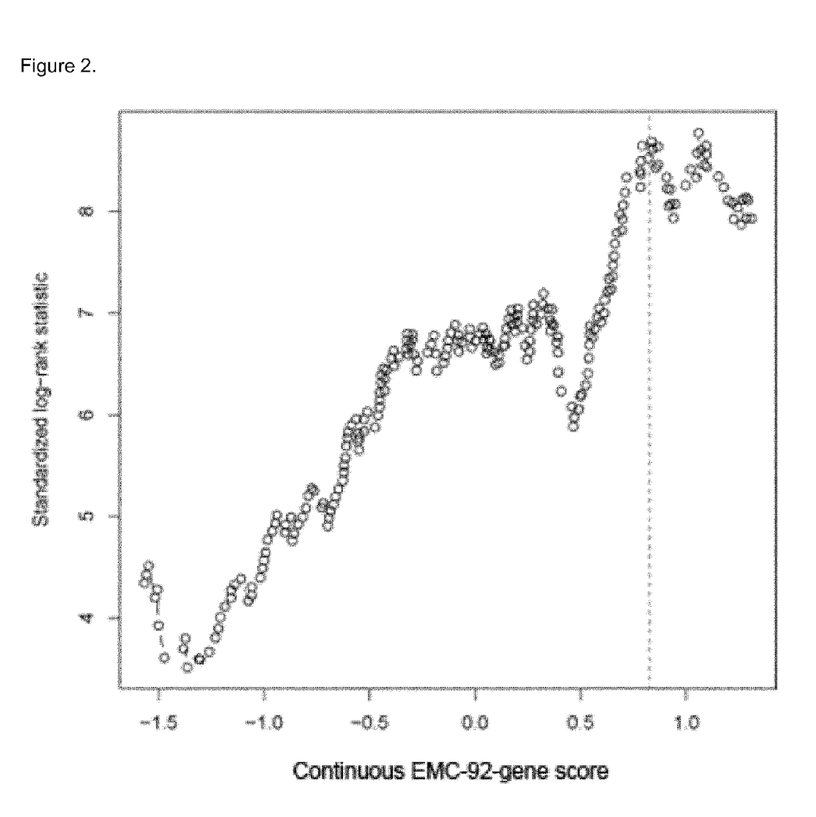
FIG. 2. Relation between threshold and log-rank performance of the EMC-92 signature in the HOVON-65/GMMG-HD4 OS. The model has an optimal performance for thresholds of at least 0.75. A cut-off for high-risk was based on defining high-risk as having an OS of <2 years within the training set which corresponded to a threshold of 0.827.

These signatures were evaluated as continuous variables as well as using the cut-off values as published (FIG. 2 and FIGS. 2a-e in reference 31, and Supplemental Documents A and B in reference 31). Overall, the performance of the EMC-92 signature was found to be robust, consistent which compares favorably with previously published signatures. Specifically, the EMC-92, UAMS, MRC-IX and GPI-50 signatures demonstrated significance in all validation sets tested both for the dichotomized and for the continuous values of the signatures. Significance was reached in three out of five studies for the IFM-15 signature using a dichotomized model, whereas the MILLENNIUM-100 signature had significant performance in the dichotomized model in one out of four independent studies. Thus, performance was less robust for the IFM-15 and MILLENNIUM-100 signatures. Although the proliferation index GPI-50 was found to be significant in all validation sets tested, the proportion of high-risk patients was much lower compared with the proportion found using either the EMC-92 or the UAMS-80 signatures. Ranked, weighted high-risk proportions are GPI: 10.0%, UAMS-17: 12.4%, UAMS-70: 13.0%, MRC-IX-6: 13.3%, EMC-92: 19.1% and UAMS-80: 23.4%. To determine which signature best explained the observed survival, pair-wise comparisons were performed. For every comparison the EMC-92 was the strongest predictor for OS tested in an independent environment (FIG. 3 and Supplemental Table S9 in reference 31).

Example 4: Combined Risk Classifiers

The performance of the EMC-92 signature was in line with the UAMS signatures, although they were derived from quite different patient populations. The intersection of high-risk patients between the EMC-92 and UAMS-70 signatures was ~8% of the total population on the pooled data sets that were independent of both our training set and the UAMS-70 training set (that is, MRC-IX, TT3 and APEX; Supplemental Table S11 in reference 31). Approximately 13% of patients were classified as high-risk by either one of these signatures. The intersecting high-risk group had the highest HR as compared with the intersecting standard-risk group (HR=3.87, 95% CI=2.76-5.42, P=3.6×10-15). Patients classified as high-risk by either signature showed an intermediate risk, that is, with a HR of 2.42, 95% CI=1.76-3.32, for the EMC-92 signature (P=5.1×10-8) and a HR of 2.22, 95% CI=1.20-4.11, for the UAMS-70 signature (P=1.1×10-2; Supplemental Table S12 in reference 31).

Example 5: EMC-92 Signature and FISH

To compare the high-risk populations composition as defined by the EMC-92 and the UAMS-70 signatures, cytogenetic aberration frequencies in both populations were determined using an independent set for which cytogenetic variables were known, that is, MRC-IX (FIG. 4 and Supplemental Table S13 in reference 31). As expected, poor prognostic cytogenetic aberrations 1q gain, del(17p), t(4; 14), t(14;16), t(14;20) and del(13q) were enriched in the high-risk populations (FIG. 5 in reference 31), whereas the standard-risk cytogenetic aberrations such as t(11;14) were diminished in the high-risk populations. In contrast, only 15% (6 out of 39) of MRC-IX cases with high-risk status as determined by the EMC-92 signature showed absence of any poor prognostic cytogenetic aberrations, as opposed to 44% (74 out of 168) in standard-risk cases (P=1.8×10-3). Similarly, of the UAMS-70-defined high-risk patients 4% (1 out of 23) did not have any poor prognostic cytogenetics, whereas of the UAMS-70 defined standard risk patients this proportion was 43%(79 out of 183) (P=5.3×10-3).

The following references are incorporated herein by reference. Their contents should be regarded as an integral part of this application.

REFERENCES

1. Greipp P R, San Miguel J, Dune B G, Crowley J J, Barlogie B, Blade J, et al. International staging system for multiple myeloma. J Clin Oncol. 2005 May 20; 23(15):3412-20.
2. Bergsagel P L, Kuehl W M. Molecular Pathogenesis and a Consequent Classification of Multiple Myeloma. J Clin Oncol. 2005 Sep. 10; 23(26):6333-8.
3. Fonseca R, Debes-Marun C S, Picken E B, Dewald G W, Bryant S C, Winkler J M, et al. The recurrent IgH translocations are highly associated with nonhyperdiploid variant multiple myeloma. Blood. 2003 Oct. 1; 102(7):2562-7.
4. Fonseca R, Hoyer J D, Aguayo P, Jalal S M, Ahmann G J, Rajkumar S V, et al. Clinical significance of the translocation (11;14)(q13;q32) in multiple myeloma. Leuk Lymphoma. 1999; 35(5-6):599-605.
5. Keats J J, Reiman T, Maxwell C A, Taylor B J, Larratt L M, Mant M J, et al. In multiple myeloma, t(4;14)(p16;q32) is an adverse prognostic factor irrespective of FGFR3 expression. Blood. 2003 Feb. 15; 101(4):1520-9.
6. Avet-Loiseau H, Malard F, Campion L, Magrangeas F, Sebban C, Lioure B, et al. Translocation t(14;16) and multiple myeloma: is it really an independent prognostic factor? Blood. 2011 Feb. 10; 117(6):2009-11.
7. Cremer F W, Bila J, Buck I, Kartal M, Hose D, Ittrich C, et al. Delineation of distinct subgroups of multiple myeloma and a model for clonal evolution based on interphase cytogenetics. Genes, chromosomes & cancer. 2005 October; 44(2):194-203.
8. Zhan F, Huang Y, Colla S, Stewart J P, Hanamura I, Gupta S, et al. The molecular classification of multiple myeloma. Blood. 2006 Sep. 15; 108(6):2020-8.
9. Broyl A, Hose D, Lokhorst H, de Knegt Y, Peeters J, Jauch A, et al. Gene expression profiling for molecular classification of multiple myeloma in newly diagnosed patients. Blood. 2010 Oct. 7; 116(14):2543-53.
10. Chng W J, Kuehl W M, Bergsagel P L, Fonseca R. Translocation t(4;14) retains prognostic significance even in the setting of high-risk molecular signature. Leukemia. 2008 February; 22(2):459-61.
11. Shaughnessy J D, Jr., Zhan F, Burington B E, Huang Y, Colla S, Hanamura I, et al. A validated gene expression model of high-risk multiple myeloma is defined by deregulated expression of genes mapping to chromosome 1. Blood. 2007 Mar. 15; 109(6):2276-84.
12. Mulligan G, Mitsiades C, Bryant B, Zhan F, Chng W J, Roels S, et al. Gene expression profiling and correlation with outcome in clinical trials of the proteasome inhibitor bortezomib. Blood. 2007 Apr. 15; 109(8):3177-88.
13. Decaux O, Lode L, Magrangeas F, Charbonnel C, Gouraud W, Jezequel P, et al. Prediction of survival in multiple myeloma based on gene expression profiles reveals cell cycle and chromosomal instability signatures in high-risk patients and hyperdiploid signatures in low-risk patients: a study of the Intergroupe Francophone du Myelome. J Clin Oncol. 2008 Oct. 10; 26(29):4798-805.
14. Dickens N J, Walker B A, Leone P E, Johnson D C, Brito J L, Zeisig A, et al. Homozygous deletion mapping in myeloma samples identifies genes and an expression signature relevant to pathogenesis and outcome. Clin Cancer Res. 2010 Mar. 15; 16(6):1856-64.
15. Hose D, Reme T, Hielscher T, Moreaux J, Messner T, Seckinger A, et al. Proliferation is a central independent prognostic factor and target for personalized and risk-adapted treatment in multiple myeloma. Haematologica. 2011 January; 96(1):87-95.
16. Sonneveld P, Schmidt-Wolf I, van der Holt B, Jarari Le, Bertsch U, Salwender H, et al. HOVON-65/GMMG-HD4 Randomized Phase III Trial Comparing Bortezomib, Doxorubicin, Dexamethasone (PAD) Vs VAD Followed by High-Dose Melphalan (HDM) and Maintenance with Bortezomib or Thalidomide In Patients with Newly Diagnosed Multiple Myeloma (MM). Blood. 2010 Nov. 19; 116(21):40-.
17. Barlogie B, Pineda-Roman M, van Rhee F, Haessler J, Anaissie E, Hollmig K, et al. Thalidomide arm of Total Therapy 2 improves complete remission duration and survival in myeloma patients with metaphase cytogenetic abnormalities. Blood. 2008 Oct. 15; 112(8):3115-21.
18. Pineda-Roman M, Zangari M, Haessler J, Anaissie E, Tricot G, van Rhee F, et al. Sustained complete remissions in multiple myeloma linked to bortezomib in total therapy 3: comparison with total therapy 2. British journal of haematology. 2008 March; 140(6):625-34.
19. Morgan G J, Davies F E, Gregory W M, Bell S E, Szubert A J, Navarro-Coy N, et al. Thalidomide Maintenance Significantly Improves Progression-Free Survival (PFS) and Overall Survival (O S) of Myeloma Patients When Effective Relapse Treatments Are Used: MRC Myeloma IX Results. Blood. 2010 Nov. 19; 116(21):623-.
20. Morgan G J, Davies F E, Owen R G, Rawstron A C, Bell S, Cocks K, et al. Thalidomide Combinations Improve Response Rates; Results from the MRC IX Study. Blood. 2007 Nov. 16; 110(11):3593-.
21. Jagannath S, Barlogie B, Berenson J, Siegel D, Irwin D, Richardson P G, et al. A phase 2 study of two doses of bortezomib in relapsed or refractory myeloma. British journal of haematology. 2004 October; 127(2):165-72.
22. Richardson P G, Barlogie B, Berenson J, Singhal S, Jagannath S, Irwin D, et al. A phase 2 study of bortezomib in relapsed, refractory myeloma. The New England journal of medicine. 2003 Jun. 26; 348(26):2609-17.
23. Richardson P G, Sonneveld P, Schuster M W, Irwin D, Stadtmauer E A, Facon T, et al. Bortezomib or high-dose dexamethasone for relapsed multiple myeloma. The New England journal of medicine. 2005 Jun. 16; 352(24):2487-98.
24. Bair E, Hastie T, Paul D, Tibshirani R. Prediction by Supervised Principal Components. J Amer Statistical Assoc. 2006 Mar. 1; 101(473):119-37.
25. Avet-Loiseau H, Magrangeas F, Moreau P, Attal M, Facon T, Anderson K, et al. Molecular Heterogeneity of Multiple Myeloma: Pathogenesis, Prognosis, and Therapeutic Implications. J Clin Oncol. 2011 May 10; 29(14):1893-7.
26. Avet-Loiseau H, Attal M, Moreau P, Charbonnel C, Garban F, Hulin C, et al. Genetic abnormalities and survival in multiple myeloma: the experience of the Intergroupe Francophone du Myelome. Blood. 2007 Apr. 15; 109(8):3489-95.
27. Fonseca R, Bergsagel P L, Drach J, Shaughnessy J, Gutierrez N, Stewart A K, et al. International Myeloma Working Group molecular classification of multiple myeloma: spotlight review. Leukemia. 2009 December; 23(12):2210-21.

28. Avet-Loiseau H, Leleu X, Roussel M, Moreau P, Guerin-Charbonnel C, Caillot D, et al. Bortezomib plus dexamethasone induction improves outcome of patients with t(4;14) myeloma but not outcome of patients with del (17p). J Clin Oncol. 2010 Oct. 20; 28(30):4630-4.
29. Neben K, Jauch A, Bertsch U, Heiss C, Hielscher T, Seckinger A, et al. Combining information regarding chromosomal aberrations t(4;14) and del(17p13) with the International Staging System classification allows stratification of myeloma patients undergoing autologous stem cell transplantation. Haematologica. 2010 July; 95(7): 1150-7.
30. Carrasco D R, Tonon G, Huang Y, Zhang Y, Sinha R, Feng B, et al. High-resolution genomic profiles define distinct clinico-pathogenetic subgroups of multiple myeloma patients. Cancer Cell. 2006; 9(4):313-25.
31. Kuiper, R. et al., Leukemia 2012, 1-8 advance on line publication, 22 Jun. 2012; doi:10.1038/leu.2012.127.

The invention claimed is:

1. A method of gene expression profiling of a multiple myeloma, the method comprising:
   contacting a probe set with a sample comprising mRNA from the multiple myeloma; and
   detecting an mRNA level for each of the genes in a set of 92 genes;
   wherein the 92 genes in the gene set are SLC30A7, AK2, SYF2, S100A6, NUF2, DARS2, ARPC5, DTL, ANGEL2, LBR, TARBP1, GGPS1, LTBP1, FAM49A, MCM6, ACVR2A, GRB14, ITGA6, DHRS9, STAT1, SPATS2L, BCS1L, SFMBT1, ARL8B, POLQ, MCM2, CCRL1, SEC62, GABRA4, PGM2, NCAPG, FGFR3, SEPT11, AIMP1, CENPE, IL7R, DHFR, SAR1B, PCDHB7, ATP6V0E1, MCM3, TUBB, MARCKS, SLC17A5, NCUBE1, SUN1/GET4, DNAJB9, RAB2A, TRAM1, ZNF252, HNRNPK, MRPL41, ZWINT, FANCF, EHBP1L1, C11orf85, PPP2R1B, ROBO3, C1S, ESPL1, ITM2B, ZBTB25, NPC2, ATPBD4, C15orf38, FANCI, SMG1, DYNLRB2, TMEM97, SPAG5, TOP2A, BIRC5, C18orf10, TSPAN16, RPS28, RPS11, NOP56, FTL, CDH22, DONSON, PFKL, ST13, DUX4, RPS4X, KIF4A, HMGN5, HMGB3, MAGEA6, the gene at chromosome 8p12 detectable with probe 208232_x_at, the gene at chromosome 11p14.1 detectable with probe 243018_at, and the gene at chromosome 11q24.3 detectable with probe 238780_s_at; and
   wherein the probe set consists of probes for the 92 genes.

2. The method according to claim 1, wherein the sample comprises plasma cells.

3. The method according to claim 1, wherein detecting the mRNA level of the 92 genes is performed utilizing a gene chip.

* * * * *